United States Patent [19]

Theodoridis

[11] Patent Number: 4,985,065
[45] Date of Patent: Jan. 15, 1991

[54] TETRAZOLINONE HERBICIDES

[75] Inventor: George Theodoridis, Princeton, N.J.

[73] Assignee: FMC Corporation, Philadelphia, Pa.

[21] Appl. No.: 349,610

[22] Filed: May 10, 1989

[51] Int. Cl.$^5$ .................. C07D 257/04; A01N 43/713
[52] U.S. Cl. ........................................ 71/92; 546/276; 548/251
[58] Field of Search ............................. 548/251; 71/92

[56] References Cited

U.S. PATENT DOCUMENTS

| | | | |
|---|---|---|---|
| 3,852,289 | 12/1974 | Mylari et al. | 544/182 |
| 3,882,115 | 5/1975 | Mylari et al. | 544/182 |
| 3,883,525 | 5/1975 | Mylari et al. | 544/182 |
| 3,883,527 | 5/1975 | Brennan | 544/182 |
| 3,883,528 | 5/1975 | Mylari et al. | 544/182 |
| 3,905,971 | 9/1975 | Miller | 544/112 |
| 4,198,407 | 4/1980 | Rosner et al. | 514/242 |
| 4,213,772 | 7/1980 | Wolf | 71/92 |
| 4,315,767 | 2/1982 | Wolf | 71/91 |
| 4,318,731 | 3/1982 | Kajioka et al. | 71/92 |
| 4,404,019 | 9/1983 | Uematsu et al. | 71/92 |
| 4,427,438 | 1/1984 | Nagano et al. | 71/92 |
| 4,431,822 | 2/1984 | Nagano et al. | 548/513 |
| 4,439,229 | 3/1984 | Swithenbank | 71/96 |
| 4,452,981 | 6/1984 | Nagano et al. | 544/236 |
| 4,640,917 | 3/1987 | Rosner et al. | 514/227.8 |
| 4,749,403 | 6/1988 | Liebl et al. | 71/90 |

FOREIGN PATENT DOCUMENTS

| | | | |
|---|---|---|---|
| 8501637 | 4/1985 | PCT Int'l Appl. | 71/92 |
| 8501939 | 5/1985 | PCT Int'l Appl. | 71/92 |
| 8602642 | 5/1986 | PCT Int'l Appl. | 71/92 |
| 1371907 | 10/1974 | United Kingdom | 544/182 |

OTHER PUBLICATIONS

Derwent Abstract, Accession No. 10224B; DT 2831770 (1979).
Derwent Abstract, Accession No. 50167E; U.S. No. 4,332,944 (1981).
Derwent Abstract, Accession No. 85-233794; J60-152,464 (1985).

Primary Examiner—Alan L. Rotman
Attorney, Agent, or Firm—Robert M. Kennedy; H. Robinson Ertelt; Abner Sheffer

[57] ABSTRACT

Herbicidal compounds of the formula

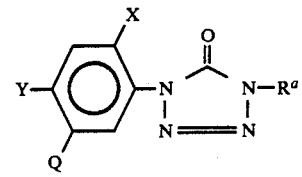

in which Q is

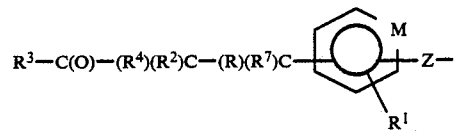

or

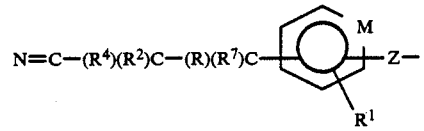

M is CH or N;
Z is O, S, NH or alkylamino;
R$^3$ is H, OH, alkoxy, alkenyloxy or alkynyloxy, alkoxyalkoxy, alkenyloxyalkoxy or alkynyloxyalkoxy, alkyl, substituted alkyl, OZ$^2$ where Z$^2$ is of a salt-forming group, amino, arylamino, alkylamino, alkenylamino, alkoxyamino, substituted alkoxyamino or —NHSO$_2$R$^5$ where R$^5$ is alkyl, haloalkyl or aryl;
R$^1$ is H, alkyl, halogen, haloalkyl, nitro, NH$_2$, lower alkoxy, alkylthio or cyano;
R$^2$ is H, lower alkyl, lower alkenyl, lower alkynyl, halogen, CN, or COR$^3$;
R is H, lower alkyl, halogen, or lower alkoxy or R and R$^2$ together constitute a double bond;
R$^4$ is H, halogen, lower alkyl, lower alkenyl, or lower alkynyl;
R$^7$ is H or lower alkyl; and
R$^a$, X and Y are so chosen that when Q is methoxy or propargyloxy, instead of Q having the formula given above, the compound is a herbicide.

27 Claims, No Drawings

TETRAZOLINONE HERBICIDES

This invention relates to novel herbicides for weed control in agriculture, horticulture and other fields where it is desired to control unwanted plant growth, such as grassy or broadleaf plant species. The invention also relates to intermediates for the production of such herbicides.

One aspect of this invention relates to herbicidal compounds of the formula

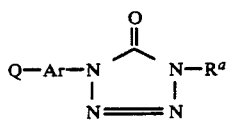

(Formula I)

where Q—Ar— is a substituted phenyl radical (e.g. of the formula

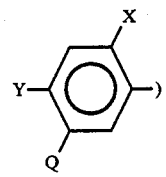

in which the substituent Q is at the 5-position (meta to the nitrogen of said formula I); Q is

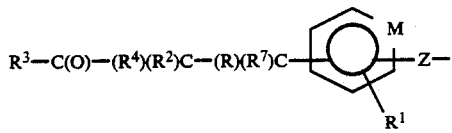

or

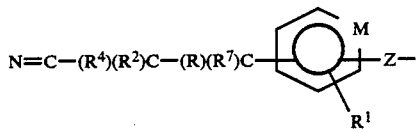

M may be CH or N.

Z may be O, S, NH or alkylamino (such as lower alkylamino, e.g. methylamino).

$R^3$ may be OH, in which case the compound is an acid, or it may be a salt, ester, amide or nitrile of such acid. Thus $R^3$ may be alkoxy (e.g. lower alkoxy such as methoxy or ethoxy), alkenyloxy or alkynyloxy (e.g. lower alkenyloxy or alkynyloxy such as allyloxy or propargyloxy), alkoxyalkoxy, alkenyloxyalkoxy or alkynyloxyalkoxy (e.g. lower alkoxyalkoxyl such as ethoxyethoxy), amino, arylamino (e.g. phenylamino), alkylamino (e.g. lower alkylamino such as methylamino or dimethylamino), alkenylamino (e.g. diallylamino), alkoxyamino (e.g. lower alkoxyamino such as methoxyamino), substituted alkoxyamino (e.g. lower alkoxyamino carrying a substituent such as lower alkoxycarbonyl as in compound 25 in Table 1 below) or a group —$NHSO_2R^5$. $R^5$ may be independently alkyl (e.g. lower alkyl such as methyl, ethyl or propyl), haloalkyl (e.g. halo lower alkyl such as trifluoromethyl) or aryl such as phenyl or substituted phenyl, (e.g. alkoxysubstituted and/or halo-substituted phenyl).

$R^3$ may also be H, in which case the compound is an aldehyde, or alkyl or substituted alkyl (e.g. methyl, ethyl or trifluoromethyl) in which case the compound is a ketone.

$R^1$ may be H, alkyl (e.g. lower alkyl such as methyl), halogen such as Cl, Br or F, haloalkyl (e.g. lower haloalkyl such as $CF_3$, $CH_2F$ or $CHF_2$), nitro, $NH_2$, lower alkoxy or alkylthio (e.g. $OCH_3$ or $SCH_3$) or cyano. There may be a plurality of $R^1$ substituents on the same benzene ring.

$R^2$ be H, lower alkyl (e.g. methyl), lower alkenyl (e.g. allyl), lower alkynyl (e.g. propargyl), halogen (e.g. Cl, Br or F), CN, or $COR^3$.

R may be H, lower alkyl (e.g. methyl), halogen (e.g. Cl or Br) or lower alkoxy (e.g. methoxy).

R and $R^2$ together may constitute a double bond.

$R^4$ may be H, halogen, lower alkyl (e.g. methyl), lower alkenyl (e.g. allyl), or lower alkynyl (e.g. propargyl).

$R^7$ may be H or lower alkyl (e.g. methyl).

In Formula I above, Ar and $R^a$ are so chosen that when Q is methoxy or propargyloxy (instead of Q having the formula given above) the compound is a herbicide. Compounds in which Q in Formula I is a methoxy or propargyloxy are, for convenience, here designated as the Methoxy Analogs and the Propargyloxy Analogs of the claimed novel compounds. Such Methoxy Analogs and Propargyloxy Analogs are well known in the art. For instance, the propargyloxy compound 1-[4-chloro-2-fluoro-5-(2-propynyloxy)phenyl]-4-(3-fluoropropyl)-5H-tetrazol-5-one is compound 121 of PCT International Application No. WO 85/01939 published May 9, 1985.

The substituent $R^a$ on the tetrazolinone ring may be any of those known in the art. For instance, $R^a$ may be lower alkyl or lower haloalkyl (e.g. fluoroalkyl); some examples of $R^a$ substituents are found in the Table below.

Preferably, "Ar" carries a substituent (i.e. other than H) at the 2-position or the 4-position of the phenyl radical, most preferably at both the 2- and 4-positions.

X may be H, halogen such as Cl, Br or F (preferably F), alkyl (e.g. lower alkyl such as methyl), haloalkyl (e.g. lower haloalkyl such as $CF_3$, $CH_2F$ or $CHF_2$) or nitro; and Y may be H, halogen such as Cl, Br or F (preferably Br or Cl), alkyl (e.g. lower alkyl such as methyl), alkoxy (e.g. lower alkoxy such as methoxy), alkylthio (e.g. lower alkylthio such as methylthio), haloalkyl (e.g. lower haloalkyl such as fluoroalkyl), —$SOCF_3$ or halo lower alkoxy such as —$OCHF_2$. Presently preferred X, Y substituents are: 2-F, 4-Cl; 2-F, 4-Br; 2,4-$Cl_2$; 2-Br, 4-Cl; and 2-F, 4-$CF_3$.

In each aspect of this invention it is often preferable that any alkyl, alkenyl, alkynyl or alkylene moiety (such as the hydrocarbon moiety of an alkoxy or haloalkoxy group) have up to about 6 carbon atoms, e.g. 1 to 4 to 5 carbon atoms, and that any cycloalkyl moiety have 3 to 7 ring carbon atoms, more preferably 3 to 6 carbon atoms.

Any acidic compound of formula I may be converted into a salt such as a sodium, potassium, calcium, ammonium, magnesium, or mono-, di or tri($C_1$ to $C_4$ alkyl)ammonium or sulfonium or sulfoxonium salt which may also be used as an herbicide. For instance the compound in which $R^3$ is OH may be thus converted into a compound in which $R^3$ is $-OZ^2$ where $Z^2$ is one of the foregoing salt-forming groups.

In the preferred compounds of this invention, $R^a$ and Ar (or X and Y) are so chosen that the Methoxy Analog or the Propargyloxy Analog of such preferred compound has marked herbicidal properties, such Analog showing at least 50% kill of at least one of the following plant species when applied under at least one of the following modes at the rate of 0.5 kg/ha, and more preferably showing such 50% kill when applied at the rate of 0.1 kg/ha:

Species: velvetleaf (*Abutilon theophrasti*) green foxtail (*Setaria viridis*); Modes: pre-emergent, postemergent. Testing for such herbicidal activity may be carried out in the manner described below (under the heading "Herbicidal Activity").

Representative compounds of this invention (including certain intermediates) are listed in Table 1.

The compounds of this invention may be prepared by the use of steps generally described in the literature or by methods analogous or similar thereto and within the skill of the art.

Many of the present herbicidal compounds may be prepared by the methods illustrated in the chemical equations below:

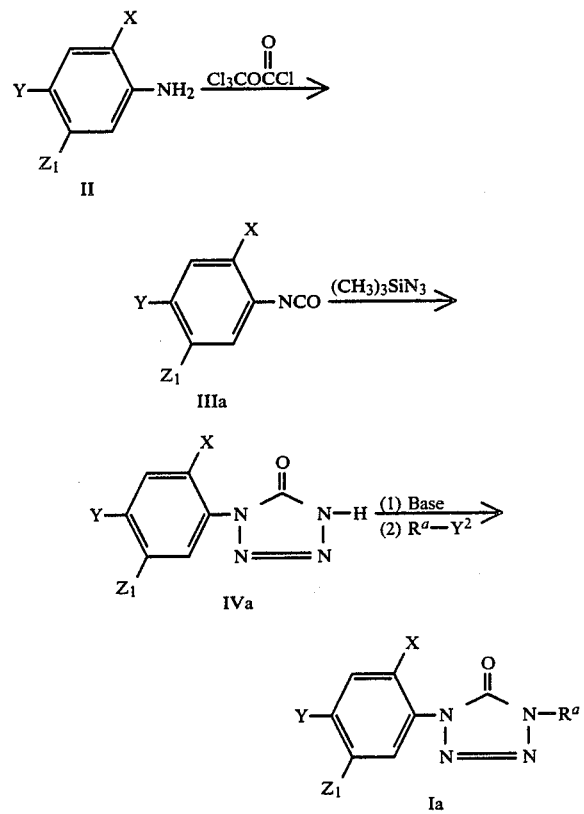

Treatment of an appropriately substituted phenylamine, II, with trichloromethyl chloroformate gives the corresponding isocyanate IIIa, which upon treatment with trimethysilyl azide in the manner of O Tsuge et al., *J. Org. Chem.*, 45, 5310 (1980), incorporated herein by reference, affords the intermediate tetrazolinone IVa. Intermediate IVa may also be prepared by treatment of he isocyanate IIIa with aluminum azide in the manner of Horwitz et al., *J. Am. Chem. Soc.*, 81, 3076 (1959), incorporated herein by reference. Treatment of the N-4 unsubstituted tetrazolinone IVa with $R^a-Y^2$, wherein $Y^2$ is a good leaving group, in the presence of a base gives compound Ia. The leaving group $Y^2$ will generally be a chlorine, bromine, or iodine atom, but may be any readily displaceable group used in the art in similar reactions. The use of sodium hydride base in N,N-dimethylformamide has been found to give satisfactory results. This method is generally useful where compound II is readily available, either coxmercially or by preparation, and is particularly useful where $Z_1$ is hydrogen, halogen, cyano, alkyl, substituted alkyl, or $-OR^1$ wherein $R^1$ is alkyl, especially lower alkyl such as methyl, or benzyl (a useful intermediate discussed below).

The OH analog (the starting material in the Example below) is readily prepared from the corresponding compound I in which $Z_1$ is a lower alkoxy group or a benzyloxy group by treatment with an acidic reagent such as concentrated sulfuric acid, concentrated hydrobromic acid, or a mixture of hydrobromic and acetic acids to effect dealkylation, or, where $Z_1$ is benzyloxy, by hydrogenolysis over palladium on charcoal ($H_2/Pd/C/C_2H_5OH$).

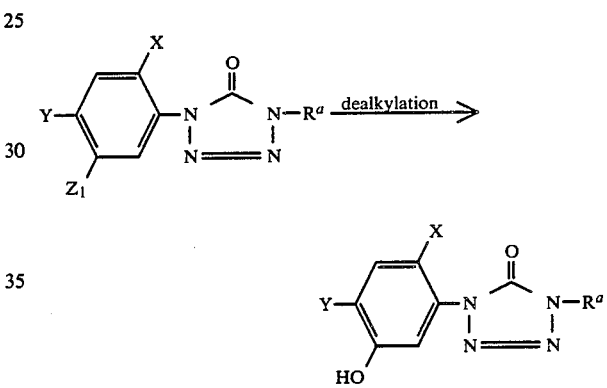

Thereafter, the Hydroxy Analog is reacted to form the nitrophenyl ether thereof, after which the nitro group is reduced to form an amino group. This amino compound is then reacted with a compound of the formula $$(R)(R^7)C=C(R^4)-C(O)-R^3$$

according to a modification of the known Meerwein reaction involving formation of a diazonium halide and its reaction with an olefin in the presence of copper halide (or according to a procedure described by Doyle *J. Org. Chem.* 243 (1977) in the presence of an alkyl nitrite and a copper (II) halide), to form a compound of the formula Formula II

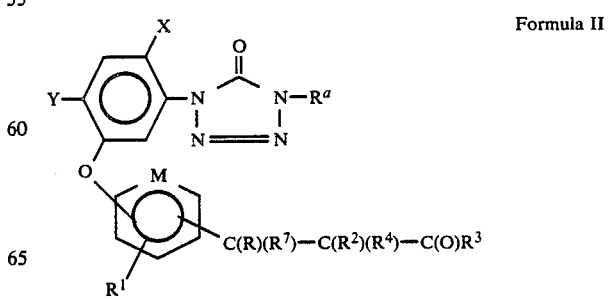

where $R^2$ is halogen.

The compound of Formula II may then be dehydrohalogenated (to produce the corresponding compound in which R and $R^2$ together constitute a double bond) and hydrogenated to produce the corresponding compound in which R and $R^2$ are each H.

As indicated above, the process involves the use of a reactant of the formula $(R)(R^7)C=C(R^4)-C(O)R^3$ or $(R)(R^7)C=C(R^4)-CN$. Among the reactants of this type which may be used are the following: methyl acrylate, ethyl acrylate, methyl methacrylate, methyl crotonate, methyl 3-chloroacrylate, methacrolein, vinylmethylketone, methacrylonitrile, acrylamide, methyl 2-methylene-4-pentenoate, and methyl 2-methylene-4-pentynoate.

Compounds of the invention in which R3 is OH, i.e. the acids, may be produced by hydrolyzing the ester (where $R^3$ is methyl, for instance). The amides (where $R^3$ is amino or substituted amino) may instance, by reacting the acid with an amine or ammonia.

The following Example is given to illustrate this invention further.

EXAMPLE

METHYL 2-CHLORO-3-[4-[2-CHLORO-4-FLUORO-5-[4-(3-FLUOROPROPYL)-1,4-DIHYDRO-5H-5-OXO-TETRAZOL-1-YL]PHENOXY]PHENYL]PROPIONATE 1-(4-chloro-2-fluoro-5-hydroxyphenyl)-4-(3-fluoropropyl)-1,4-dihydro-5H-tetrazol-5-one is etherified with 4-fluoronitrobenzene in the presence of potassium carbonate in N,N-dimethylformamide to form 1-[4-chloro-2-fluoro-5-(4-nitrophenoxy)phenyl]-4-(3-fluoropropyl)-1,4-dihydro-5H-tetrazol-5-one (Compound A). Compound A is then reduced with iron powder in acetic acid and water to produce 1-[5-(4-aminophenoxy)-4-chloro-2-fluorophenyl]-4-(3-fluoropropyl)-1,4-dihydro-5H-tetrazol-5-one (Compound B). Acetone is added to a stirring mixture of Compound B in hydrochloric acid. The mixture is cooled to about 5° C., and a solution of an equimolar amount of sodium nitrite in water and a molar excess of methyl acrylate are added in succession. The resultant mixture is stirred for 15–20 minutes, after which copper (I) chloride is slowly added. The mixture is stirred at room temperature for approximately 30 minutes and then poured into ice water. The resulting mixture is then treated with an organic solvent (e.g., ethyl acetate) to extract the product, methyl 2-chloro-3-[4-[2-chloro-4-fluoro-5-[4-(3-fluoropropyl)-1,4-dihydro-5H-5-oxo-tetrazol-1-yl]phenoxy]phenyl]propionate, which may then be purified, as by column chromatography on silica gel.

HERBICIDAL ACTIVITY

The plant test species used in demonstrating the herbicidal activity of compounds of this invention include cotton (*Gossypium hirsutum* var. DPL61), soybean (*Glycine max* var. Williams), field corn (*Zea mays* var. Pioneer 3732), wheat (*Triticum aestivium* var. Wheaton), rice (*Orvza sativa* var. Labelle), morningglory (*Ipomea lacumosa* or *Ipomea hederacea*), wild mustard (*Brassica kaber*), velvetleaf (*Abutilon theophrasti*), barnyardgrass (*Echinochloa crus-galli*), green foxtail (*Setaria viridis*), and johnsongrass (*Sorghum halepense*).

Preparation of Flats

Preemergence

Two disposable fiber flats (8 cm×15 cm×25 cm) for each rate of application for each candidate herbicide for preemergence testing are filled to an approximate depth of 6.5 cm with steam sterilized sandy loam soil. The soil is leveled and impressed with a template to provide six evenly spaced furrows 13 cm long and 0.5 cm deep in each flat. Seeds of cotton, soybean, corn, rice and wheat are planted in five of the furrows of the first flat (the sixth furrow is left unplanted), and seeds of wild mustard, morningglory, velvetleaf, barnyardgrass, green foxtail, and johnsongrass are planted in the six furrows of the second flat. The template is again employed to firmly press the seeds into place. A topping soil of equal portions of sand and sandy loam soil is placed uniformly on top of each flat to a depth of approximately 0.5 cm. The flats are first watered, then sprayed with a solution of test compound as described below.

Postemergence

Two flats for each rate of application for each herbicide candidate are also prepared for postemergence application. The postemergence flats are prepared in the same manner as discussed above for the preemergence flats. The prepared flats are watered for 8–11 days then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24 g/4 flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/has rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed , B. Truelove, Ed.; Southern Weed Science Society; Auburn University, Auburn, Ala., 1977. The rating system is as follows:

Herbicide Rating System

| Rating Percent Control | Description of Main Categories | Crop Description | Weed Description |
|---|---|---|---|
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 0.8 parts of the herbicidal compound, 17.9 parts of Palmetto clay, and 1.0 part of sodium lignosulfonate and 0.3 part of sulfonated aliphatic polyester as wetting agents. Other wettable powder formulations are:

| Component: | % by Wt. |
|---|---|
| Active ingredient | 40.00 |
| Sodium lignosulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate 2% powdered sodium lignosulfonate 2% powdered anionic sodium alkylnaphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| Oil Suspension: | % by Wt. |
|---|---|
| Active ingredient | 25.00 |
| Polyoxyethylene sorbitol hexaoleate | 5.00 |
| Highly aliphatic hydrocarbon oil | 70.00 |
| Total | 100.00 |

| Aqueous Suspension: | % by Wt. |
|---|---|
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as 5 g/ha or less, e.g. about 5 to 250 g/ha postemergently. For field use, where there are losses of herbicide, higher application rates (e.g. four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4(3H)-one-2,2-dioxide (bentazon); triazine herbicides such as 6-chloro-N-ethyl-N-(1-methylethyl)-3,5-triazine-2,4-diamine (atrazine), and 2-[4-chloro-6-(ethylamino)-1,3,5-triazin-2-yl]amino-2-methyl-propanenitrile (cyanazine); dinitroaniline herbicides such as 2,6-dinitro-N,N-dipropyl-4-(trifluoromethyl)- benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

In each of the foregoing compounds 1-51 the $Q^1$ substituent is para to the oxygen atom. Other representative compounds are identical with each of compounds 1-51 above except that $Q^1$ is at the meta position (with any $R^1$ substituent being in the para position). Still other representative compounds are identical with each of compounds 1-51 except that $Q^1$ is at an ortho position.

Other representative compounds are identical with the foregoing compounds 1-51, respectively, except

TABLE

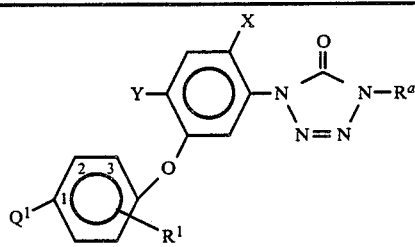

| Cmpd. No. | $R^a$ | X | Y | $R^1$ | $Q^1$ |
|---|---|---|---|---|---|
| 1 | $CH_2CH_2CH_2F$ | F | Cl | H | $CH_2CH(Cl)COOCH_3$ |
| 2 | $CH_2CH_2CH_2F$ | F | Cl | H | $CH_2C(CH_3)(Cl)COOCH_3$ |
| 3 | $CH_2CH_2CH_2F$ | F | Cl | H | $CH_2C(CH_3)(Cl)C(O)H$ |
| 4 | $CH_2CH_2CH_2F$ | F | Cl | 3-F | $CH_2C(CH_3)(Cl)COOH$ |
| 5 | $CH_2CH_2CH_2F$ | F | Cl | 3-Cl | $CH_2C(CH_3)(Cl)COOH$ |
| 6 | $CH_2CH_2CH_2F$ | F | Cl | 3-F | $CH_2C(Cl_2)COOH$ |
| 7 | $CH_2CH_2CH_2F$ | F | Cl | 3-F | $CH_2CH(Cl)COOCH_3$ |
| 8 | $CH_2CH_2CH_2F$ | F | Cl | 3-Cl | $CH_2CH(Cl)COOCH_3$ |
| 9 | $CH_2CH_2CH_2F$ | F | Cl | 3-F | $CH_2C(CH_3)(Cl)COOCH_3$ |
| 10 | $CH_2CH_2CH_2F$ | F | Cl | 3-Cl | $CH_2C(CH_3)(Cl)COOCH_3$ |
| 11 | $CH_2CH_2CH_2F$ | F | Cl | 3-F | $CH_2C(CH_3)(Cl)COOC_2H_5$ |
| 12 | $CH_2CH_2CH_2F$ | F | Cl | 3-F | $CH_2C(CH_3)(Cl)COOCH(CH_3)_2$ |
| 13 | $CH_2CH_2CH_2F$ | F | Cl | 3-F | $CH_2C(CH_3)(Cl)COO(CH_2)_2OC_2H_5$ |
| 14 | $CH_2CH_2CH_2F$ | F | Cl | 3-F | $CH_2CH(CH_3)COOCH_3$ |
| 15 | $CH_2CH_2CH_2F$ | F | Cl | 3-F | $CH(CH_3)CH(Cl)COOCH_3$ |
| 16 | $CH_2CH_2CH_2F$ | F | Cl | 3-F | $CH_2C(CH_3)(Br)COOCH_3$ |
| 17 | $CH_2CH_2CH_2F$ | F | Cl | 3-F | $CH(CH_3)C(CH_3)(Cl)COOCH_3$ |
| 18 | $CH_2CH_2CH_2F$ | F | Cl | $3-CF_3$ | $CH_2C(CH_3)(Cl)COOCH_3$ |
| 19 | $CH_2CH_2CH_2F$ | F | Cl | $2-COOCH_3$ | $CH_2C(CH_3)(Cl)COOCH_3$ |
| 20 | $CH_2CH_2CH_2F$ | F | Cl | 3-F | $CH=C(CH_3)COOCH_3$ |
| 21 | $CH_2CH_2CH_2F$ | F | Cl | 3-F | $CH_2CH(Cl)CONH_2$ |
| 22 | $CH_2CH_2CH_2F$ | F | Cl | 3-F | $CH_2CH(Cl)CON(CH_3)_2$ |
| 23 | $CH_2CH_2CH_2F$ | F | Cl | 3-F | $CH_2C(CH_3)(Cl)CONHCH_3$ |
| 24 | $CH_2CH_2CH_2F$ | F | Cl | 3-F | $CH2(CH_3)(Cl)CONHCH(CH_3)_2$ |
| 25 | $CH_2CH_2CH_2F$ | F | Cl | 3-F | $CH_2CH(Cl)CONHCH(OCH_3)$<br>$\quad\quad\quad\quad\quad\quad\quad\quad\ \ \|$<br>$\quad\quad\quad\quad\quad\quad\quad\quad COOCH_3$ |
| 26 | $CH_2CH_2CH_2F$ | F | Br | H | $CH_2CH(CH_3)CO_2CH_3$ |
| 27 | $CH_2CH_2CH_2F$ | F | Br | 3-Cl | $CH_2CH(CH_3)CO_2CH_3$ |
| 28 | $CH_2CH_2CH_2F$ | F | Br | 3-F | $CH_2CH(CH_3)CO_2CH_3$ |
| 29 | $CH_2CH_2CH_2F$ | F | Br | $3-CH_3$ | $CH_2CH(CH_3)CO_2CH_3$ |
| 30 | $CH_2CH_2CH_2F$ | F | Br | $3-CF_3$ | $CH_2CH(CH_3)CO_2CH_3$ |
| 31 | $CH_2CH_2CH_2F$ | F | Br | $3-NO_2$ | $CH_2CH(CH_3)CO_2CH_3$ |
| 32 | $CH_2CH_2CH_2F$ | F | $CF_3$ | H | $CH_2CH(CH_3)CO_2CH_3$ |
| 33 | $CH_2CH_2CH_2F$ | F | $CF_3$ | 3-Cl | $CH_2CH(CH_3)CO_2CH_3$ |
| 34 | $CH_2CH_2CH_2F$ | F | $CF_3$ | 3-F | $CH_2CH(CH_3)CO_2CH_3$ |
| 35 | $CH_2CH_2CH_2F$ | Cl | Cl | H | $CH_2CH(CH_3)CO_2CH_3$ |
| 36 | $CH_2CH_2CH_2F$ | Cl | Cl | 3-Cl | $CH_2CH(CH_3)CO_2CH_3$ |
| 37 | $CH_2CH_2CH_2F$ | Cl | Cl | 3-F | $CH_2CH(CH_3)CO_2CH_3$ |
| 38 | $CH_2CH_2CH_2F$ | Cl | Cl | $3-CH_3$ | $CH_2CH(CH_3)CO_2CH_3$ |
| 39 | $CH_2CH_2CH_2F$ | Cl | Cl | $3-CF_3$ | $CH_2CH(CH_3)CO_2CH_3$ |
| 40 | $CH_2CH_2CH_2F$ | Cl | Cl | $3-NO_2$ | $CH_2CH(CH_3)CO_2CH_3$ |
| 41 | $CH_2CH_2CH_2F$ | F | Cl | H | $CH_2CH(CH_3)CO_2Na$ |
| 42 | $CH_2CH_2CH_2F$ | F | Cl | H | $CH_2CH(CH_3)CN$ |
| 43 | $CH_2CH_2CH_2F$ | F | Cl | H | $CH_2CH(CH_3)COCH_3$ |
| 44 | $CH_2CH_2CH_2F$ | F | Cl | H | $CH_2CH(CH_3)CONHSO_2CH_3$ |
| 45 | $CH_3$ | F | Cl | 3-Cl | $CH_2CH(CH_3)CO_2CH_3$ |
| 46 | $C_2H_5$ | F | Cl | 3-Cl | $CH_2CH(CH_3)CO_2CH_3$ |
| 47 | $n-C_3H_7$ | F | Cl | 3-Cl | $CH_2CH(CH_3)CO_2CH_3$ |
| 48 | $iso-C_3H_7$ | F | Cl | 3-Cl | $CH_2CH(CH_3)CO_2CH_3$ |
| 49 | $CH_2CH_2F$ | F | Cl | 3-Cl | $CH_2CH(CH_3)CO_2CH_3$ |
| 50 | $CH_2CH=CH_2$ | F | Cl | 3-Cl | $CH_2CH(CH_3)CO_2CH_3$ |
| 51 | $CH_2CH_2CF_2H$ | F | Cl | 3-Cl | $CH_2CH(CH_3)CO_2CH_3$ | that in each case the aromatic ring bearing the $Q^1$ substituent is a pyridine ring of the formula

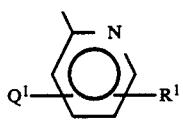

with the $Q^1$ and $R^1$ being in the respect to the free valence (connected to O) as in said compounds 1-51.

I claim:

1. A herbicidal compound of the formula

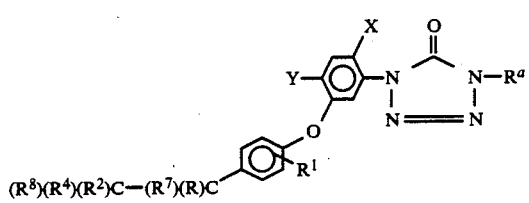

in which $R^a$ is alkyl, haloalkyl, or alkenyl;

X is H, halogen, alkyl, or haloalkyl;

Y is H, halogen, alkyl, alkoxy, alkylthio, haloalkyl, —SOCF$_3$, or haloalkoxy;

$R^1$ is H, alkyl, halogen, haloalkyl, nitro, alkoxy, alkylthio, or CN;

R is H, alkyl, halogen, or alkoxy;

$R^7$ is H or alkyl;

$R^2$ is H, alkyl, alkenyl, alkynyl, halogen, CN, COR$^3$; or $R^2$ together with R constitutes a double bond;

$R^4$ is H, halogen, alkyl, alkenyl, or alkynyl;

$R^8$ is CN or COR$^3$; and $R^3$ is OH, alkoxy, alkenyloxy, alkynyloxy, alkoxyalkoxy, alkenyloxyalkoxy, alkynyloxyalkoxy, amino, phenylamino, alkylamino, alkenylamino, alkoxyamino, alkoxycarbonyl substituted alkoxyamino, —NHSO$_2$R$^5$ in which R$^5$ is alkyl, haloalkyl, phenyl, halophenyl or alkoxyphenyl, or —OZ$^2$ where Z$^2$ is a monovalent salt-forming cation; and in which each occurrence of the terms alkyl, alkenyl, alkynyl, alkoxy, alkenyloxy, alkynyloxy, including prefixes and suffixes, have up to six carbon atoms.

2. A herbicidal compound as in claim 1 in which X and Y are halogen.

3. A herbicidal compound as in claim 1 in which $R^a$ is alkyl or haloalkyl and $R^8$ is C(O)R$^3$.

4. A herbicidal compound as in claim 3 in which $R^a$ is haloalkyl.

5. Herbicidal compound as in claim 3 in which X is F or Cl and Y is Cl or Br.

6. A herbicidal compound as in claim 5 in which the compound is an acid in which $R^3$ is OH or a salt or ester of said acid.

7. A herbicidal compound as in claim 6 in which $R^2$ is halogen.

8. A herbicidal compound as in claim 6 in which $R^2$ is methyl.

9. A herbicidal compound as in claim 6 in which R and $R^2$ together constitute a double bond.

10. A herbicidal composition comprising a herbicidally effective amount of the compound of claim 1 in admixture with a suitable carrier.

11. A method for controlling undesired plant growth which comprises applying to the locus where control is desired a herbicidally effective amount of the composition of claim 10.

12. A herbicidal composition comprising a herbicidally effective amount of the compound of claim 2 in admixture with a suitable carrier.

13. A method for controlling undesired plant growth which comprises applying to the locus where control is desired a herbicidally effective amount of the composition of claim 12.

14. A herbicidal composition comprising a herbicidally effective amount of the compound of claim 3 in admixture with a suitable carrier.

15. A method for controlling undesired plant growth which comprises applying to the locus where control is desired a herbicidally effective amount of the composition of claim 14.

16. A herbicidal composition comprising a herbicidally effective amount of the compound of claim 4 in admixture with a suitable carrier.

17. A method for controlling undesired plant growth which comprises applying to the locus where control is desired a herbicidally effective amount of the composition of claim 16.

18. A herbicidal composition comprising a herbicidally effective amount of the compound of claim 5 in admixture with a suitable carrier.

19. A method for controlling undesired plant growth which comprises applying to the locus where control is desired a herbicidally effective amount of the composition of claim 18.

20. A herbicidal composition comprising a herbicidally effective amount of the compound of claim 6 in admixture with a suitable carrier.

21. A method for controlling undesired plant growth which comprises applying to the locus where control is desired a herbicidally effective amount of the composition of claim 2.

22. A herbicidal composition comprising a herbicidally effective amount of the compound of claim 7 in admixture with a suitable carrier.

23. A method for controlling undesired plant growth which comprises applying to the locus where control is desired a herbicidally effective amount of the composition of claim 22.

24. A herbicidal composition comprising a herbicidally effective amount of the compound of claim 8 in admixture with a suitable carrier.

25. A method for controlling undesired plant growth which comprises applying to the locus where control is desired a herbicidally effective amount of the composition of claim 24.

26. A herbicidal composition comprising a herbicidally effective amount of the compound of claim 9 in admixture with a suitable carrier.

27. A method for controlling undesired plant growth which comprises applying to the locus where control is desired a herbicidally effective amount of the composition of claim 26.

* * * * *